US007741031B2

(12) United States Patent
Kramer et al.

(10) Patent No.: US 7,741,031 B2
(45) Date of Patent: Jun. 22, 2010

(54) OPTICALLY DECODABLE MICROCARRIES, ARRAYS AND METHODS

(75) Inventors: Fred R. Kramer, Riverdale, NY (US); Sanjay Tyagi, New York, NY (US); Salvatore A. E. Marras, Jersey City, NJ (US); Hiyam Elhajj Trunfio, New York, NY (US)

(73) Assignee: The Public Health Research Institute of the City of New York, Newark, NJ (US)

( * ) Notice: Subject to any disclaimer, the term of this patent is extended or adjusted under 35 U.S.C. 154(b) by 573 days.

(21) Appl. No.: 10/791,502

(22) Filed: Mar. 2, 2004

(65) Prior Publication Data

US 2004/0248163 A1    Dec. 9, 2004

Related U.S. Application Data

(60) Provisional application No. 60/452,667, filed on Mar. 7, 2003.

(51) Int. Cl.
*C12Q 1/68* (2006.01)
(52) U.S. Cl. ........................................ 435/6
(58) Field of Classification Search ........................ None
See application file for complete search history.

(56) References Cited

U.S. PATENT DOCUMENTS

| 5,312,728 | A | * | 5/1994 | Lizardi et al. | 435/6 |
| 5,607,834 | A | | 3/1997 | Bagwell | |
| 5,925,517 | A | | 7/1999 | Tyagi et al. | |
| 6,150,097 | A | | 11/2000 | Tyagi et al. | |
| 6,331,438 | B1 | | 12/2001 | Aylott et al. | |
| 6,500,622 | B2 | * | 12/2002 | Bruchez et al. | 435/6 |
| 6,579,680 | B2 | * | 6/2003 | Frutos et al. | 435/6 |
| 6,680,377 | B1 | * | 1/2004 | Stanton et al. | 536/22.1 |
| 6,844,154 | B2 | * | 1/2005 | Landers | 435/6 |
| 6,890,741 | B2 | * | 5/2005 | Fan et al. | 435/91.2 |

FOREIGN PATENT DOCUMENTS

WO    WO/00/14278    3/2000
WO    WO01/46675 A2    6/2001

OTHER PUBLICATIONS

Liu et al. (2000) Analytical Biochemistry 283:56-63.*
V. A. Bloomfield, D. M. Crothers and I. Tinoco, Jr., *Nucleic Acids: Structure, Properties, and Functions* (1999); Ch. 8, pp. 258-333 entitled "Conformational Changes", by D. H. Turner.
D. Freifelder, *Physical Biochemistry, Second Edition* (1982) "The Concept of Native and Denatured Structures"; pp. 19-29.
Adessi, et al. "Solid phase DNA amplification: characterisation of primer attachment and amplification mechanisms" *Nucleic Acids Research*, (2000) vol. 28, No. 20 e87.
Albert et al, "Automatic decoding of sensor types within randomly ordered, high-density optical sensor arrays" *Analytical and Bioanalytical Chemistry*, (Aug. 2002) vol. 373, No. 8, pp: 792-802.

Bonnet, et al. "Thermodynamic basis of the enhanced specificity of structured DNA probes", *Proc. Natl. Acad. Sci.* (May 1999) vol. 96, pp. 6171-6176.
Braeckmans, et al. "Encoding Microcarriers: Present and Future Technologies" *Nature Publishing Group, Nature Reviews*, (Jun. 2002) vol. 1 pp. 447-456.
Brenner et al. "Gene expression analysis by massively parallel signature sequencing (MPSS) on microbead arrays" *Nature Biotechnology*, (Jun. 2000) vol. 18, pp: 630-634.
Brown, et al. "Molecular beacons attached to glass beads fluoresce upon hybridisation to target DNA" *Chem. Commun.* (2000), 621-622.
Call, et al. "Fabrication of DNA Microarrays Using Unmodified Oligonucleotide Probes" *Bio Techniques*, (Feb. 2001) 30: 368-379.
Chen, et al. "A Microsphere-Based Assay for Multiplexed Single Nucleotide Polymorphism Analysis Using Single Base Chain Extension" *Genome Research* (2000) 10: 549-557.
Danowski, et al. "Evaluating the chemical spatial resolution of imaging fiber chemical sensors" *Microchemical Journal* (2001) 70: 51-61.
Dickinson, et al. "Convergent, Self-Encoded Bead Sensor Arrays in the Design of an Artificial Nose" *Analytical Chemistry*, (Jun. 1, 1999) 71: 2192-2198.
Epstein, et al. "High-Density Fiber-Optic Genosensor Microsphere Array Capable of Zeptomole Detection Limits" *Analytical Chemistry* (2002) 74: 1836-1840.
Epstein, et al. "Combinatorial Decoding: An approach for Universal DNA Array Fabrication" *J. Am. Chem. Soc.* (2003) 125: 13753-13759.
Ferguson, et al. "A fiber-optic DNA biosensor microarray for the analysis of gene expression" *Nature Biotechnology* (Dec. 1996) 14: 1681-1684.
Ferguson, et al. "High-Density Fiber-Optic DNA Random Microsphere Array" *Analytical Chemistry* (Nov. 2000) 72: 5618-5624.
Guo, et al. "Direct fluorescence analysis of genetic polymorphisms by hybridization with oligonucleotide arrays on glass supports" *Nucleic Acids Research*, (1994) 22: 5456-5465.
Han, et al. "Quantum-dot tagged microbeads for multiplexed optical coding of biomolecules" *Neuter. Biotechnology* (Jul. 2001) 19: 631-635.
Kellar, et al. "Multiplexed microsphere-based flow cytometric assays" *Experimental Hematology* (2002) 30: 1227-1237.

(Continued)

*Primary Examiner*—Heather G Calamita
(74) *Attorney, Agent, or Firm*—Fox Rothschild LLP; Gerard P. Norton; Vyacheslav Vasilyev (57) ABSTRACT

A coding scheme for microcarriers suitable for use in distributed arrays includes labeling the carriers with quenched signaling hairpin molecules with any one of three to eight distinguishable fluorophores wherein the hairpins are of at least two types, most preferably three types, that open and fluoresce differentially as a chemical or physical condition, for example temperature, is changed. Mixtures of microcarriers having immobilized capture probes can be decoded by measuring fluorescence from said fluorophores under conditions under which only one type of hairpin is open, under which two types of hairpin are open, and so on. Mixtures of coded microcarriers with capture probes are used in assays for nucleic acids utilizing microarray methods.

22 Claims, 10 Drawing Sheets

OTHER PUBLICATIONS

Lee, et al. "Importance of replication in microarray gene expression studies: Statistical methods and evidence from repetitive cDNA hybridizations" *PNAS* (Aug. 29, 2000) 97: 9834-9839.

Liu, et al. "Molecular Beacons for DNA Biosensors with Micrometer to Submicrometer Dimensions" *Analytical Biochemistry* (2000) 283: 56-63.

Lui, et al. "A fiber-Optic Evanescent Wave DNA Biosensor Based on Novel Molecular Beacons" *Analytical Chemistry* (1999) 71: 5054-5059.

Marras, et al. "Efficiencies of fluorescence resonance energy transfer and contact-mediated quenching in oligonucleotide probes" *Nucleic Acids Research* (2002) 30: e122.

Michael, et al. "Randomly Ordered Addressable High-Density Optical Sensor Arrays" *Analytical Chemistry* (1998) 70: 1242-1248.

Miller, Kelli "Downsizing DNA Assays—Pharmaseq's microtransponders prove that bigger isn't always better" *The Scientist* (2002) 16[1]: 52.

Nicewamer-Pena, et al. "Submicrometer Metallic Barcodes" *Science* (2001) 294: 137-141.

Oliphant, et al. "BeadArray™ Technology: Enabling an Accurate, Cost-Effective Approach to High-Throughput Genotyping" *BioTechniques* (Jun. 2002) 32: S56-S61.

Rosenthal, Sandra J. "Bar-coding biomolecules with fluorescent nanocrystals" *Nature Biotechnology* (2001) 19: 621-622.

Spiro, et al. "A Bead-Based Method for Multiplexed Identification and Quantitation of DNA Sequences Using Flow Cytometry" *Applied and Environmental Microbiology* (2000) 66: 4258-4265.

Spruill, et al. "Assessing Sources of Variability in Microarray Gene Expression Data" *BioTechniques* (2002) 33: 916-923.

Steemers, et al. "Screening unlabeled DNA targets with randomly ordered fiber-optic gene arrays" *Nature Biotechnology* (2000) 18: 91-94.

Tsagkatakis, et al. "Spatial and Spectral Imaging of Single Micrometer-Sized Solvent Cast Fluorescent Plasticized Ploy(vinyl chloride) Sensing Particles" *Analytical Chemistry* (2001) 73:315320.

Tyagi et al, "Molecular Beacons: Probes that Fluoresce upon Hybridization" *Nature Biotechnology* (1996) 14: 303-308.

Tyagi et al. "Multicolor molecular beacons for allele discrimination" *Nature Biotechnology* (1998) 16: 49-53.

Tyagi et al. "Taking a census of mRNA populations with microbeads" *Nature Biotechnology* (2000) 18: 597-598.

Walt, David R. "Bead-based Fiber-Optic Arrays" *Science* (2000) 287: 451-452.

Walt, David R. "Imaging optical sensor arrays" *Current Opinion in Chemical Biology* (Oct. 2002) 6: 689-695.

Yang, et al. "BADGE, BeadsArray for the Detection of Gene Expression, a High-Throughput Diagnostic Bioassay" *Genome Research* (2001) 11: 1888-1898.

Yeakley, et al. "Profiling alternative splicing on fiber-optic arrays" *Nature Biotechnology* (2002) 20: 353-358.

PharmaSeq, Inc. "Animation: Principle of Microtransponder-Based Assay" htti://www.pharmaseq.com/tech.html#desc (pp. 1-3), 2009.

* cited by examiner

| Sequence | SEQ ID NO: | Name | Fluorophore | Quencher | Actual Tm (°C) |
|---|---|---|---|---|---|
| CGCTCT CTCTCTGAGTCT AGAGCG | 1 | TM62 | FAM | dabcyl | 64 |
| CGCCG TCTGTCTGAGTCT CGGCG | 2 | TM68 | FAM | dabcyl | 67.5 |
| CGACCTGG CTGTCTGACT CCAGGTCG | 3 | TM74 | FAM | dabcyl | 73 |
| CGGACGCG CTGTCTGAGTC CGCGTCCG | 4 | TM80 | FAM | dabcyl | 80 |
| CCCGCCC TATGTCTGAGTC GGGCGGGG | 5 | TM86 | FAM | dabcyl | 82 |
| GGTG CTGTCTGAGTCT CACC | 6 | TM47 | TET | dabcyl | 50 |
| ATGGG TGTCTGAGTCT CCCAT | 7 | TM60 | TET | dabcyl | 58.5 |
| CGCTCG GTCTGTCTGAGTCTAT CGAGCG | 8 | TM72 | TET | dabcyl | 68 |
| AGGACGCG CTGTCTGAGTC CGCGTCCT | 9 | TM85 | TET | dabcyl | 79 |
| CCCCGCCCG CTGTCTGAGTC CGGGCGGGG | 10 | TM90 | TET | dabcyl | 84.5 |
| CGCCCGCCCG CTGTCTGAGTC CGGGCGGGGCG | 11 | TM93 | TET | dabcyl | 88.5 |
| ATGGG TGTCTGAGTCT CCCAT | 7 | TM60 | A546 | dabcyl | 58 |
| ATGGG TGTCTGAGTCT CCCAT | 7 | TM60.B | A546 | BHQ2 | 66 |
| CGACCTGG CTGTCTGACT CCAGGTCG | 3 | TM74 | A546 | dabcyl | 74 |
| CCCGCCCC TATGTCTGAGTC GGGCGGGG | 5 | TM86.C | A546 | BHQ2 | 84 |
| CCCCGCCCG CTGTCTGAGTC CGGGCGGGG | 10 | TM90 | A546 | dabcyl | 86 |
| ATGGG TGTCTGAGTCT CCCAT | 7 | TM60 | Texas red | dabcyl | 64 |
| CGCTCG GTCTGTCTGAGTCTAT CGAGCG | 8 | TM72 | Texas red | dabcyl | 75.5 |
| AGGACGCG CTGTCTGAGTC CGCGTCCT | 9 | TM85 | Texas red | dabcyl | 84 |
| CCCGCCCC TATGTCTGAGTC GGGCGGGG | 5 | TM86.A | Texas red | dabcyl | 87 |
| CGCCCGCCCG CTGTCTGAGTC CGGGCGGGG | 11 | TM93 | Texas red | dabcyl | 91 |
| ATGGG TGTCTGAGTCT CCCAT | 7 | TM60 | TAMRA | dabcyl | 59 |
| CGACCTGG CTGTCTGACT CCAGGTCG | 3 | TM74 | TAMRA | dabcyl | 75 |
| AGGACGCG CTGTCTGAGTC CGCGTCCT | 9 | TM85 | TAMRA | dabcyl | 81 |
| CGCCCGCCCG CTGTCTGAGTC CGGGCGGGG | 11 | TM93 | TAMRA | dabcyl | 91 |
| CCCCGCCCG CTGTCTGAGTC CGGGCGGGG | 10 | TM90 | TAMRA | dabcyl | 87 |

OPTICALLY DECODABLE MICROCARRIES, ARRAYS AND METHODS

This application claims the benefit under 35 United States Code, Section 119(e)(1) of U.S. provisional application 60/452,667, filed Mar. 7, 2003.

TECHNICAL FIELD

This invention relates to coding and decoding microcarriers, particularly mixtures of microbeads having immobilized hybridization probes, and arrays of such microcarriers, particularly distributed arrays.

BACKGROUND

The use of arrays for detection and identification of biological and chemical substances is known. An example is fixed nucleic acid hybridization arrays that contain a multiplicity of different hybridization probes immobilized at separate known locations on a planar solid surface, for example a silicon chip or glass slide. At each location in the array, many copies of the same hybridization probe are immobilized. Planar arrays can contain hundreds or even thousands of different areas, each with immobilized hybridization probes. When an analyte containing nucleic acids is added to the array, different nucleic acid sequences will hybridize to probes in different locations. Detection of hybridization at a particular location indicates the presence of a nucleic acid sequence in the sample being analyzed that is complementary to the sequence of the probe immobilized at that location. In general, arrays of this type are prepared in one of two ways: either probes are synthesized in place, as by photolithography techniques, or probes are pre-synthesized and then immobilized. Detection of hybridization is accomplished in any of several ways, including attaching detection labels to analyte substances prior to the hybridization step, addition of an intercalating dye that fluoresces when in contact with double-stranded nucleic acid, adding color-forming moieties to analyte substances for use in a subsequent color-generating step, or by performing sandwich hybridizations in which the targets are bound to capture probes on the array and labeled detector probes are hybridized to the bound targets. It has been found that surface microarrays are subject to substantial variation. Lee, M.-L. T. et al. (2000), Importance of Replication in Microarray Gene Expression Studies: Statistical Methods and Evidence from Repetitive cDNA Hybridizations, Proc. Natl. Acad. Sci. USA 97: 9834-9839.

Another type of array utilizes microcarriers, for example microbeads, having immobilized on their surfaces capture substances, such as hybridization probes for nucleic acids. Individual beads are coated with one or another hybridization probe, and analyte is contacted with a mixture containing at least one bead, generally multiple beads, containing each probe sequence. The beads can be slurried with analyte, which overcomes some of the variation encountered with planar arrays, and then laid down in a planar array of microbeads. Alternatively, the microbeads can be laid down into a planar array prior to contact with analyte. Microbeads may be contacted with analyte, washed and settled into a microscope slide as a planar array. The planar array may also be a pair of narrowly separated transparent plates which trap microbeads in a single layer and are part of a flow cell through which analyte and wash solutions may be flowed. Brenner, S. et al. (2000), Gene Expression Analysis by Massively Parallel Signature Sequencing (MPSS) on Microbead Arrays, Nat. Biotechnol. 18: 630-634. Microbeads can also be settled into depressions etched in the ends of individual strands of a fiber-optic cable bundle containing a large number of strands. Ferguson, J. A. et al. (1996), A Fiber-Optic DNA Biosensor Microarray for the Analysis of Gene Expression, Nat. Biotechnol. 14: 1681-1684. In such distributed arrays, where location does not identify which probe is present, coding schemes are required so that beads containing particular probes can be identified. Rather than laying beads down in a planar array, flow cytometry can be used to interrogate individual beads using, for example, a fluorescence-activated cell sorter. Here again, coding schemes are required.

Simply labeling beads with differently colored fluorophores does not provide a sufficient code, because fewer than ten, practically only seven or eight, different fluorophores can be distinguished. Several complex bead-coding methods have been devised. One coding scheme has been to imbed combinations of fluorophores in the beads. Combinations of colors and intensity comprise a code. Spiro, A. et al. (2000), A Bead-Based Method for Multiplexed Identification and Quantitation of DNA Sequences Using Flow Cytometry, Appl. Environ. Microbiol. 66: 4258-4265. Multiple stimulations and readings of laser light at different wavelengths interrogate each bead to read its code. This scheme requires substantial equipment, cannot deconvolve spectra in real time, and has been limited to about one hundred differently coded beads. Another coding scheme is to imbed tiny stripes of different metals into microcarriers and read the metallic pattern in each microcarrier. This scheme involves complicated microcarrier manufacturing. Another scheme is to embed in each microcarrier a miniature transponder that is energizable by a photocell and transmits a fifty-digit binary code for identification. Such microcarriers can be flowed by a station to detect hybridization and a separate station to decode the microcarrier. A drawback with this transponder scheme is that the microcarriers are not true spheres and fluorescence is to some extent a function of a bead's orientation as it passes a detection station.

Immobilized oligonucleotides have been used for coding purposes. One such system utilizes sixteen different oligonucleotides for coding. Coding is accomplished by deciding in advance, for each of the sixteen types of coding oligonucleotides, whether or not that particular type of coding oligonucleotide will be immobilized on the surface of a given type of bead. Since there are sixteen choices to be made, one for each coding oligonucleotide, the number of different codes (and thus the number of different types of beads) is 2 raised to the power 16, which is 65,536. Beads in a mixture are first fixed to the ends of fiber optic strands in a bundle. The remote ends of the strands are attached to a detector in a fixed pattern. Through a series of sixteen different hybridization reactions with labeled probes, each bead is interrogated and the identity of each bead associated with its fiber optic strand is determined. The bundle can then be contacted with analyte. Oliphant et al. (2002), BeadAway™ Technology: Enabling an Accurate, Cost-Effective Approach to High-Throughput Genotyping, BioTechniques 32: S56-S61. Schemes relying on a serial hybridization are complicated, cumbersome and expensive.

An aspect of this invention is a bead-coding scheme that combines detectable fluorescent labels with a physically induced change in fluorescence to permit coding and optical decoding of hundreds and even thousands of different beads.

Another aspect of this invention is hybridization array methods and reagents, including particularly distributed array methods and reagents, utilizing such a combination coding scheme.

Another aspect of this invention is the use of a coded microcarrrier having immobilized on its surface a plurality of quenched, labeled signaling hairpin molecules each comprising an interacting affinity pair separated by a linking moiety, one member of the affinity pair having bound thereto at least one fluorophore and the other member of the affinity pair having bound thereto at least one quencher, wherein interaction of the affinity pair of each hairpin molecule is disruptable by a physical or chemical change in a condition of its environment, wherein the disruption of the interaction of at least one affinity pair occurs at a first level of said condition and the disruption of at least another affinity pair occurs at a second level of said condition, and where said disruptions are optically differentiable.

Another aspect of this invention is the use in a distributed microarray of a mixture of a plurality of coded microcarriers according to the preceding paragraph, wherein the individual microcarriers each have immobilized thereon a capture probe and wherein the coding scheme for identifying individual microcarriers in said mixture comprises a combination of from three to eight spectrally differentiable fluorophores and at least three affinity pairs disruptable at detectably different levels of said condition, optionally where there is a plurality of identically coded microcarriers having immobilized thereon the same capture probe, and optionally wherein the capture probes are molecular beacon probes.

SUMMARY

This invention provides a bead-coding scheme by which hundreds and, if desired, thousands and tens of thousands of differently coded beads can be simply and easily labeled and rapidly and accurately decoded. The coding reagents comprise signaling hairpins immobilized on the surface of the beads. A signaling hairpin is an extended molecule labeled with a pair of labeling moieties which change intensity of optical signal depending on whether or not they are interacting, preferably at least one fluorophore on one end and a quencher on the other end that forms a hairpin structure in which fluorescence is quenched. The molecule can undergo a conformational rearrangement such that the fluorophores and quencher are separated, in which event the fluorophore's fluorescence is not quenched. One type of suitable molecule is similar to molecular beacon probes, which are described in, for example, Tyagi et al. U.S. Pat. No. 5,925,517, which is incorporated by reference herein in its entirety. Quenching can be by fluorescence resonance energy transfer (FRET), as disclosed in said patent or by physical interaction, as disclosed in Tyagi et al. U.S. Pat. No. 6,150,097, which is also incorporated by reference herein in its entirety. Dabcyl is an example of a quencher that can quench by physical interaction. Commercially available "Black Hole Quenchers" are another example.

The hairpin probes disclosed in U.S. Pat. No. 5,925,517 comprise a single-stranded oligonucleotide loop flanked by a pair of moieties, an "affinity pair," that interact with each other and create the hairpin structure. One type of affinity pair is oligonucleotide sequences that hybridize to each other to form a double-stranded stem. Other affinity pairs disclosed therein include protein-ligand, antibody-antigen, protein subunits, and nucleic acid binding proteins-binding sites. Certain quenchers can themselves form an affinity pair with a fluorophore. Forming or disrupting the affinity pair changes the conformation of the probe and its fluorescence intensity, changes an optical signal from another type of label pair, or changes signal generation from an at least temporarily localized reaction, such as color formation, as disclosed in U.S. Pat. No. 5,925,517. Absorbance rather than emission can also be measured. A typical example of such a probe is a "molecular beacon probe," an oligonucleotide having a central single-stranded region ("loop") complementary to an intended target, flanked by complementary sequences ("arms") that hybridize to one another, forming a hairpin conformation in which a quencher on one arm quenches the fluorescence of a fluorophore on the other arm. Hybridization of the loop to its target overcomes the stem hybrid and separates the fluorophore from the quencher, thereby significantly reducing their interaction and producing fluorescence. However, as disclosed in U.S. Pat. No. 5,925,517, a molecular beacon probe can also be changed from its closed, hairpin conformation to an open, random-coil conformation by heating the probe to denature the stem hybrid.

A signaling hairpin useful in this invention has similarities to a molecular beacon probe. It is a molecule having a central single-stranded loop that assumes a hairpin structure due to interaction of a flanking affinity pair whose interaction can be disrupted by a controllable physical or chemical change in its environment. The loop portion of the molecule functions as a linker separating the affinity pair. It need not, and in preferred embodiments does not, function as a probe. The central linking moiety may be a nucleic acid sequence, a carbon chain, or any other molecular structure capable of opening and closing as a loop. The affinity pair is a pair of interacting moieties that are capable of causing the molecule to assume a hairpin configuration under preselected hybridization assay conditions during use, but whose interaction can be disrupted by a physical or chemical change in its environment. For example, when the affinity pair comprises complementary arms that form a stem hybrid, that stem hybrid can be disrupted by an increase in temperature, a lowering of salt concentration, or addition of a denaturing reagent, for example, formamide. The hairpin includes at least one fluorophore associated with one member of the affinity pair and at least one quencher associated with the other member of the affinity pair, such that disruption of the interaction of the affinity pair causes the signaling hairpin to fluoresce when stimulated. As indicated earlier, in some cases a fluorophore-quencher pair may double as an affinity pair.

The coding scheme of this invention involves the use of multiple signaling hairpins whose affinity pairs are disrupted under different conditions. For example, preferred signaling hairpins have complementary oligonucleotide arms that can readily be constructed to melt at a desired temperature. A series of three or more such molecules can be constructed to melt at three different temperatures, for example, 50° C., 60° C. and 70° C. If a hybridization assay temperature of, for example, 40° C. is utilized, all three signaling hairpins will be closed due to their affinity pairs, and all will be quenched. However, if the temperature is raised progressively, first one hairpin will open (50° C.), then a second (60° C.), then a third (70° C.). Fluorescence will change with temperature. The same effect, that is, a discernable change in fluorescence intensity, will occur at a constant temperature through a progressive change in the chemical environment, for example, an increase in concentration of a denaturant such as formamide, or a decrease in concentration of a salt such as guanidine thiocyanate. In preferred embodiments, the effect of the physical or chemical change is reversible, and the hairpins can be reused.

The coding scheme of this invention also involves the use of multiple fluorophores. Available detection equipment can deconvolve complex spectra into the spectral contributions of between two to eight differently colored fluorophores, in some cases even more, for example nine or ten differently colored fluorophores.

The coding scheme of this invention involves immobilizing on microbeads a selection of different signaling hairpins which in combination uniquely identify each bead type. For example, if one begins with three hairpin structures identifiable by a physical or chemical change in their environment, and one begins with five differently colored fluorophores, then fifteen different signaling hairpins can be synthesized (five differently colored signaling molecules for each of the three physically or chemically distinguishable hairpins). Coding is accomplished by deciding in advance, for each of the fifteen types of signaling hairpin, whether or not that particular type of signaling hairpin will be immobilized on the surface of a given type of bead. Since there are fifteen choices to be made, one for each signaling hairpin, the number of different codes (and thus the number of different types of beads) is 2 raised to the power 15, which is 32,768. If one then immobilizes on each bead type a unique hybridization probe, one has up to 32,768 coded hybridization probes.

It will be appreciated that coding beads according to this invention is simple and straightforward. Depending on the size of the desired array, only two or three different hairpin molecules need be constructed, although one might utilize a higher number for example four or five. Oligonucleotide molecules can be synthesized with a quencher on one end and a functionalized nucleotide on the other end. Glen Research (Sterling, Va., USA) sells supports (columns) for use in oligonucleotide synthesizers that already include a quencher such as dabcyl. To complete the labels, stocks of only several fluorophores need be maintained. Addition of fluorophores and immobilization of the signaling hairpins can be accomplished by well-known methods on suitable microbeads, such as glass or polystyrene microbeads. In order to link signaling hairpins to the surfaces of microbeads, either the fluorophore or the quencher can be placed at an internal location within the signaling hairpin. A functional group, such as a primary amino group, sulfhydryl group, or biotin group, can then be covalently linked to the available terminus of the signaling hairpin. Tyagi S. et al. (2000), Wavelength-Shifting Molecular Beacons, Nat. Biotechnol. 18: 1191-1196. These functional groups can then be used to link the signaling hairpin to the surfaces of microbeads that are modified to contain either succinimydal ester groups, maleamide groups, or streptavidin molecules. A simple incubation of the functionalized signaling hairpin with microbeads containing the appropriate linking group on their surface will join the signaling hairpins to the surface of the microbeads. The design of hairpin-forming oligonucleotides can be accomplished by methods well known for molecular beacon probes. Design of other hairpin molecules and attachment of other affinity pairs is within the skill of the art. Manufacture and immobilization of hybridization probes is well known in the art.

Coded hybridization microbeads according to this invention can be utilized in known assay methods and systems. One preferred embodiment is to slurry coded microbeads containing unlabeled hybridization probes, sometimes referred to as capture probes, in an analyte solution in which nucleic acid target molecules, DNA or cDNA or mRNA for example, are labeled so as to be optically detectable. We prefer fluorescent labels. The labels of analyte molecules need not be different: a single label, preferably different from any coding label, suffices. Our most preferred embodiment is to utilize fluorophore/quencher-labeled molecular beacon probes as hybridization probes, Molecular beacon probes open and become unquenched when they hybridize to their target. Molecular beacon probes immobilized on the surface of the microbeads can be molecular beacons, each labeled with same fluorophore. This invention is not limited to any particular method of detecting whether some analyte molecule, or target, has hybridized to a bead. Any other suitable optical detection system and method for recognizing target hybridization can be used, for example, a modified sandwich assay as disclosed in Spiro et al. Also, subsequent physical or enzymatic modification of the probe-target hybrids can be performed, for example, the enzymatic addition of a single fluorescently labeled nucleotide to the 3' end of the probe, in order to discern the presence of a single nucleotide polymorphism in the captured target strand. Chen J. et al. (2000), A Microsphere-Based Assay for Multiplexed Single Nucleotide Polymorphism Analysis Using Single Base Chain Extension, Genome Research 10: 549:557. After hybridization is complete, the beads can be settled onto a microscope slide or other suitable surface, stimulated by light of an appropriate wavelength, and "read" utilizing known and available epifluorescence microscopic equipment capable of pattern recognition. This identifies which beads have found targets. Decoding according to this invention identifies which beads those are and, from knowledge of their production, which hybridization sequences they contain. If, for example, the signaling hairpins are constructed to melt at 58, 72 and 82° C., and the analyte hybridization is carried out at 50° C., the temperature of the slide can be raised to 88° C. at a rate suitable for the instrumentation, such as a few degrees a minute, and real-time fluorescence curves can be obtained for each bead. Computer programs can rapidly deconvolve the data from each microbead into the fluorescence contribution due to each fluorophore at each temperature interval, and computer programs can rapidly calculate the rate of change of fluorescence intensity (I) with respect to changes in temperature (T) for each fluorophore, so that peaks in the plot of dI/dT versus T for each differently colored fluorophore used to label the signal hairpins will indicate which signaling hairpins are present on each microbead in the visual field, thus identifying each bead and, hence, each hybridized sequence in the analyte being tested. Variable temperature heating apparatus is well known for laboratory equipment. For example, the heating blocks of standard thermal cyclers can readily be adapted for use on the stage of an epifluorescence microscope.

Another preferred embodiment of hybridization assays utilizing mixtures of coded beads according to this invention is the Brenner et al. method of assembling distributed planar arrays of microbeads in a flow cell, either prior to or subsequent to mixing with analyte. Beads in the assembled array can first be read for hybridization and then be decoded. For example, the temperature can be increased progressively, as described above. Alternatively a solution gradient can be flowed through the cell, for example a solution or solutions containing increasing concentrations of a denaturants such as formamide or urea, or decreasing concentrations of salts such as guanidine thiocyanate or sodium trifluoroacetate, which will cause shorter stem hybrids to open first and the longest, or more accurately strongest, stem hybrids to open last, once again giving a fluorescence pattern discernable by available equipment. Any assay in which analyte hybridization to a particular bead can be detected and in which that bead can be kept track of and decoded is suitable for use in this invention.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 2A-2C show the melting behavior of an embodiment of a signaling hairpin molecule useful in this invention.

DETAILED DESCRIPTION

Figure 1:
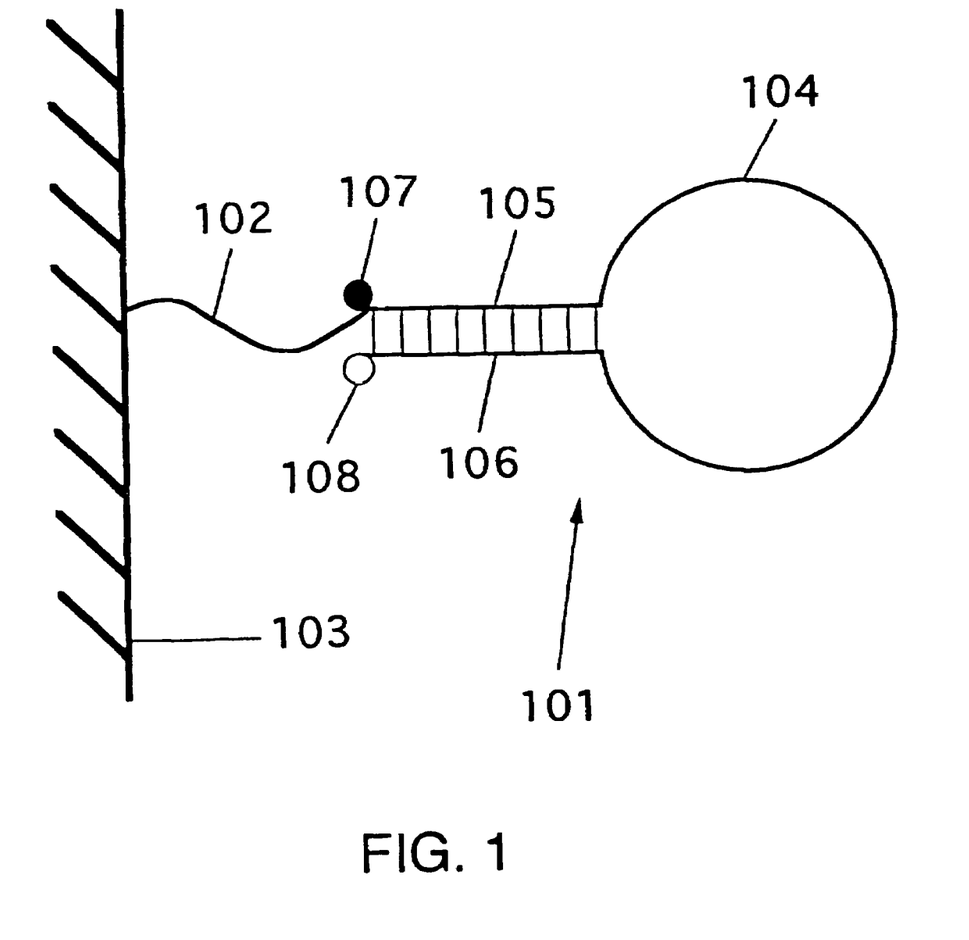
FIG. 1 is a stylized depiction of an embodiment of a signaling hairpin molecule useful in this invention immobilized to the surface of a bead.

FIG. 1 depicts an embodiment of an immobilized signaling hairpin 101 according to this invention. Hairpin molecule 101 comprises a central linking moiety 104 flanked by an affinity pair 105, 106, shown as complementary oligonucleotide sequences. Central linking moiety may also be an oligonucleotide, but as stated above, need not be. If linking moiety 104 is an oligonucleotide sequence, we prefer that hairpin 101 not function as a hybridization probe in intended hybridization assays. Oligonucleotide arms 105, 106 can be DNA, RNA or combinations thereof. Arms 105, 106 can include non-natural nucleotides, modified nucleotides, and modified inter-nucleotide linkages. The same applies to central linking moiety 104, if it is an oligonucleotide sequence. Although we prefer complementary oligonucleotide arms as the affinity pair, any pair of moieties that interact by reversibly binding to each other under assay conditions, and whose interaction can be disrupted by a either a physical or chemical change in their environment, can be used in signaling hairpins according to this invention. Connected to affinity-pair members 105 is a quencher moiety 107. Connected to affinity-pair member 106 is fluorophore 108. Moieties 107, 108 are positioned and attached such that when hairpin 101 is in the position shown, fluorescence from fluorophore 108 is highly quenched, and disruption of affinity pair 105, 106 separates fluorophore 108 from quencher 107 sufficiently that fluorescence is much less quenched. Multiple quencher moieties can be included, as can multiple fluorophore moieties, including a pair of fluorophores that interact by FRET. The fluorophore 108 and the quencher 107 can be any pair of chemical moieties that alter the intensity of a detectable signal that they produce, depending on whether the affinity pair are bound to each other or not bound to each other. As earlier indicated, in some embodiments moieties 107, 108 can comprise at least a portion of the affinity pair.

In our most preferred embodiments, the affinity pair and the linking moiety are an oligonucleotide which can be readily synthesized using, for example, an oligonucleotide synthesizer. Design of such structures is well known from the design of molecular beacon probes. See, for example, U.S. Pat. No. 5,925,517; U.S. Pat. No. 6,150,097; Tyagi, S. and Kramer, F. R. (1996), Molecular Beacons: Probes that Fluoresce upon Hybridization, Nat. Biotechnol. 14: 303-308; Tyagi et al. (1998), Multicolor Molecular Beacons for Allele Discrimination, Nat. Biotechnol. 16: 49-53; Marras et al. (2002), Efficiencies of Fluorescence Resonance Energy Transfer and Contact-Mediated Quenching in Oligonucleotide Probes, Nucleic Acids Res. 30: e122; Bonnet, G et al. (1999), Thermodynamic Basis of the Enhanced Specificity of Structured DNA Probes, Proc. Natl. Acad. Sci. USA 96: 6171-6176. Each of these references is incorporated herein in its entirety.

As shown in FIG. 1, hairpin 101 is immobilized on solid surface 103, for example the surface of a glass or polystyrene microbead, through linker 102, covalent attachment of molecules, including nucleic acid molecules, to solid surfaces is well known. Adessi, C. et al. (2003), Solid Phase DNA Amplification: Characterization of Primer Attachment and Amplification Mechanisms, Nucleic Acids Res. 28: e87; Call, D. R. et al. (2001), Fabrication of DNA Microarrays Using Unmodified Oligonucleotide Probes, BioTechniques 30: 368-379; Guo, Z. et al. (1994), Direct Fluorescence Analysis of Genetic Polymorphisms by Hybridization with Oligonucleotide Arrays on Glass Supports, Nucleic Acids Res. 22: 5456-5465. References specifically disclosing attachment of hairpin structures, namely molecular beacon probes, include Brown L. J. et al. (2000), Molecular Beacons Attached to Glass Beads Fluoresce upon Hybridization to Target DNA, Chem. Comm. 2000: 621-622; Liu, X. and Tan, W. (1999), A Fiber-Optic Evanescent Wave DNA Biosensor Based on Novel Molecular Beacons, Anal. Chem. 71: 5054-5059; Liu, X. et al. (2000), Molecular Beacons for DNA Biosensors With Micrometer to Submicrometer Dimensions, Anal. Biochem. 283: 56063; Steemers, F. J. et al. (2000), Screening Unlabeled DNA Targets with Randomly Ordered Fiber-Optic Gene Arrays, Nat. Biotechnol. 18: 91-94, each of which is incorporated by reference herein in its entirety.

Solid surface 103 can be the surface of any suitable microcarrier. Our preferred embodiments utilize microbeads, which may be of any suitable material, for example, glass or an organic polymer such as polystyrene. Depending on how the microcarrier is to be read, its optical properties may be required to fit system requirements, for example transparency.

Figure 2A:
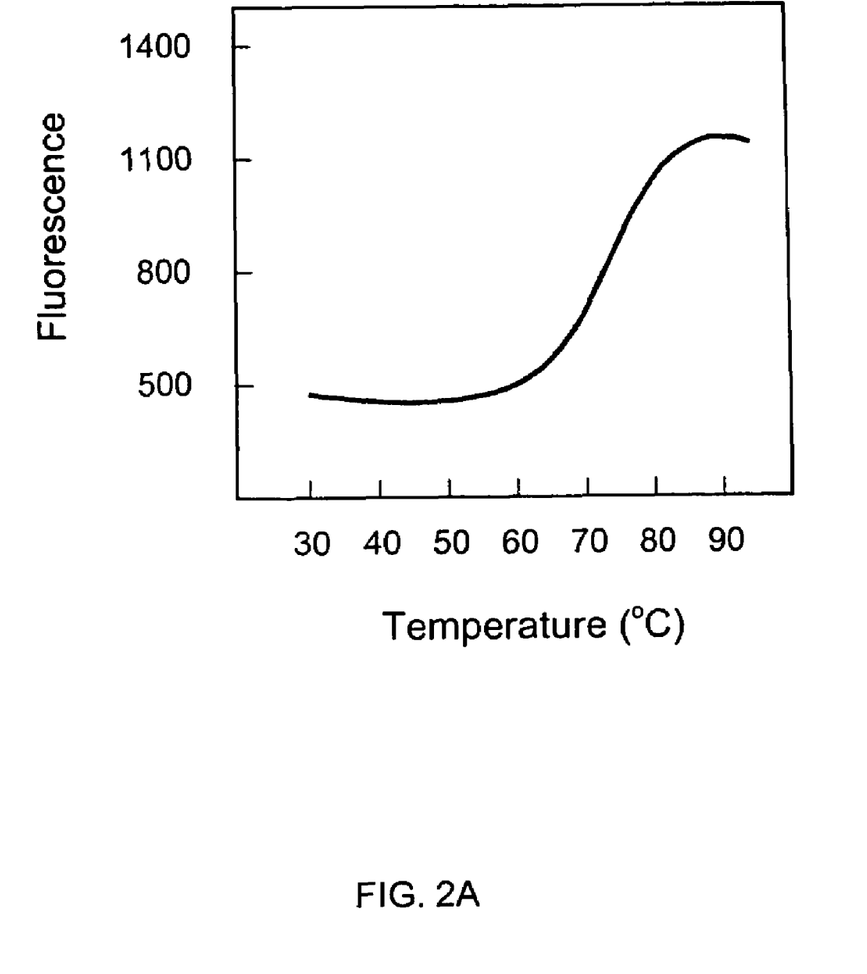
FIG. 2A is a signal hairpins's melting curve.
Figure 2B:
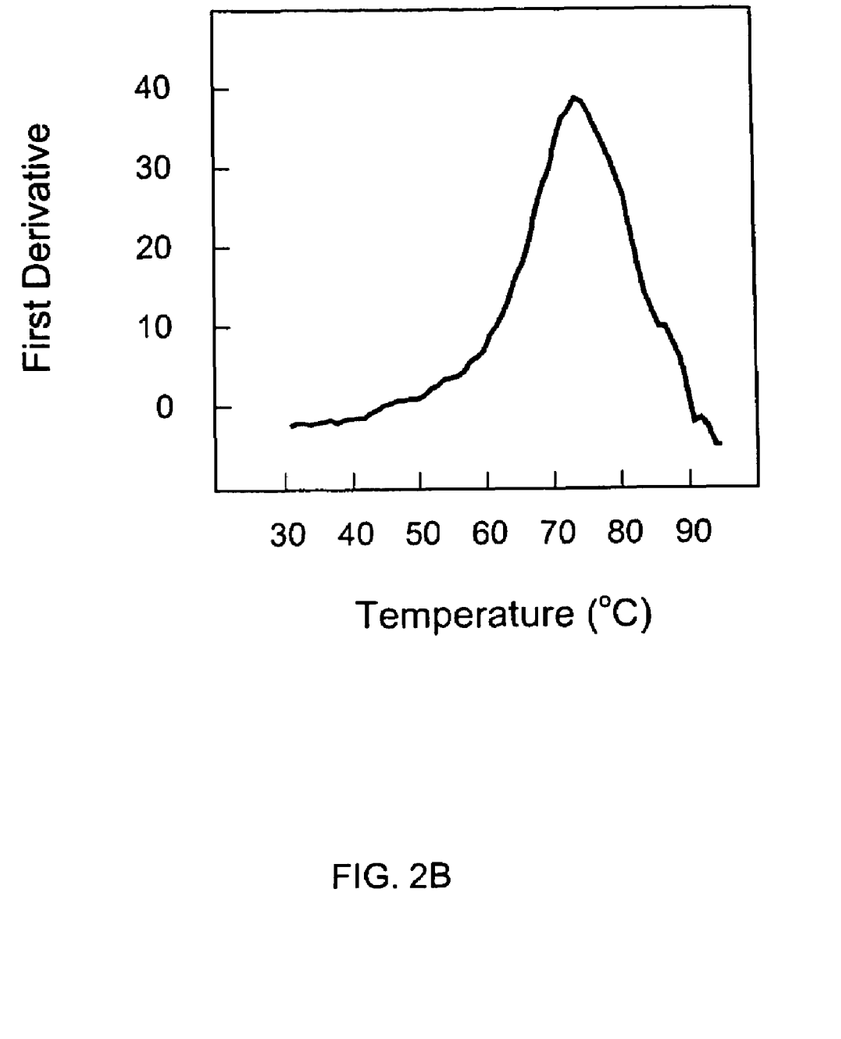
FIG. 2B is the first derivative of the melting curve.
Figure 2C:
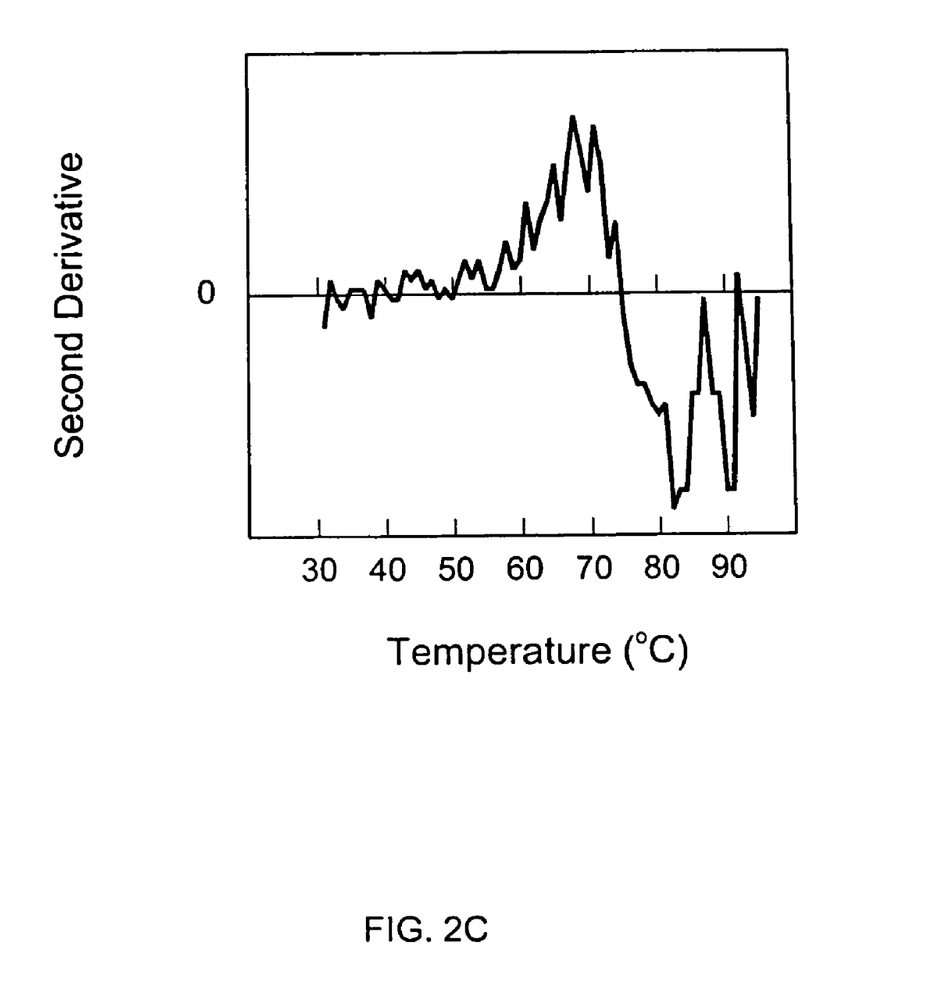
FIG. 2C is the second derivative of the melting curve.

FIGS. 2A-2C show the melting behavior of an oligonucleotide signaling hairpin having complementary arms as an affinity pair, labeled with a fluorophore and quencher. FIG. 2A shows fluorescence intensity as a function of temperature. The signaling hairpin was Texas red-labeled TM72. FIG. 2B shows the first derivative of the curve of FIG. 2A, and FIG. 2C shows the second derivative. The first derivative yields a steep peak at the melting point, while the second derivative yields positive and negative peaks beside the melting point, which is where the trace passes through zero. We find the first derivative most useful for use in decoding.

Figure 3:
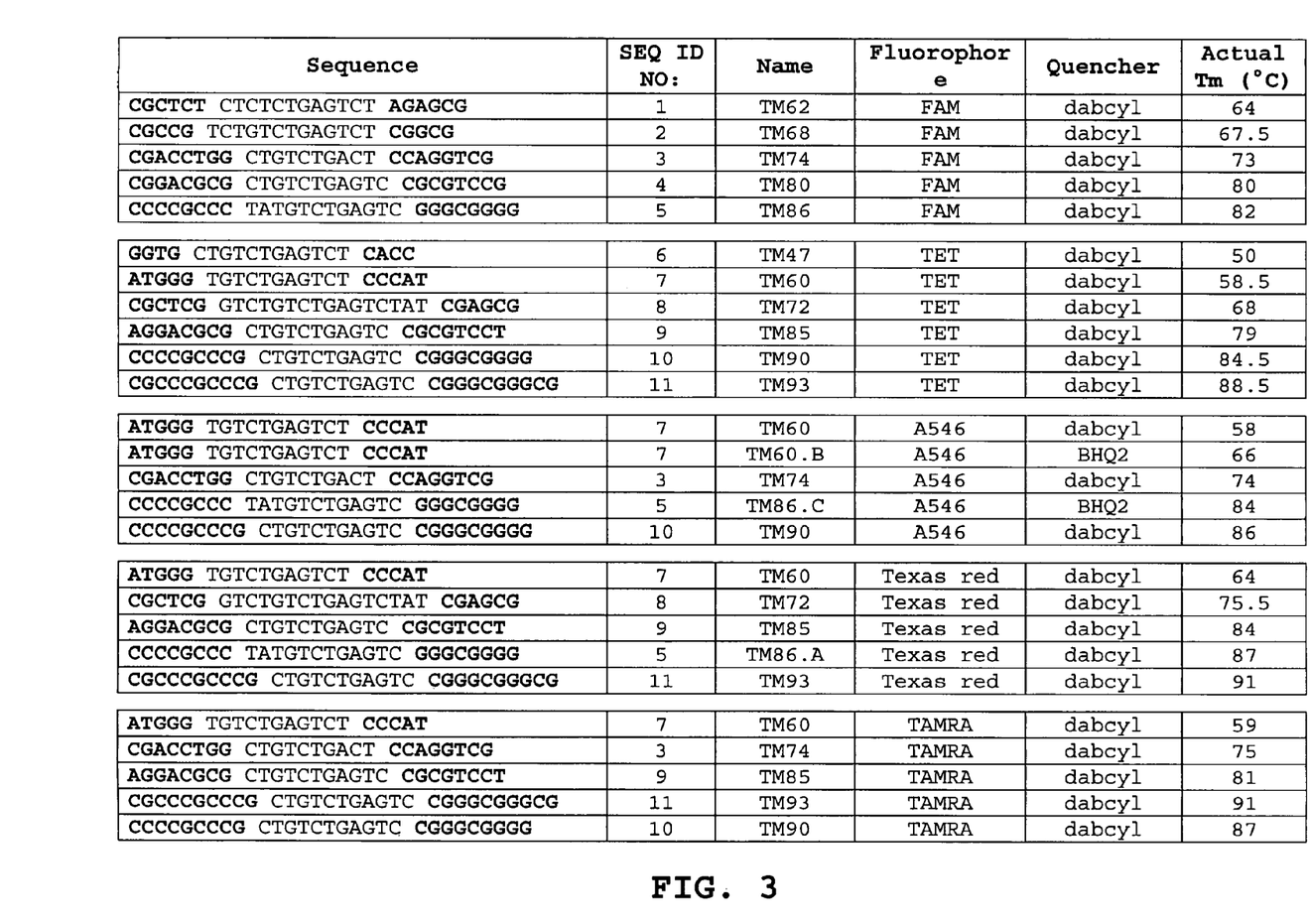
FIG. 3 is a chart showing the sequences, sequence identification numbers, labeling, and melting temperatures of a number of signaling hairpin oligonucleotide molecules that have been made and tested.

We have designed a number of signaling hairpins having differing melting points for use in coding according to this invention. FIG. 3 identifies several of those hairpins, gives their sequences (the complementary arms are in bold), and melting points determined under a possible assay condition: 50 µl of 1×PCR buffer (Applied Biosystems) plus 4 mM $MgCl_2$. Melting curves were obtained by reducing the temperature from 95° C. to 23° C. at a rate of 1° C. every 30 seconds. Data was collected every degree. The hairpins were all terminally labeled with a fluorophore and a quencher, as shown in FIG. 1. As a quencher, we generally utilized dabcyl, although we also utilized Black Hole Quencher No. 2 (for hairpins TM60.B and TM86.C). As FIG. 3 shows, designs having linkers (loops) 9-12 nucleotides long coupled to arms of varying lengths provided a range of melting temperatures spanning 40° C.

Figure 4:
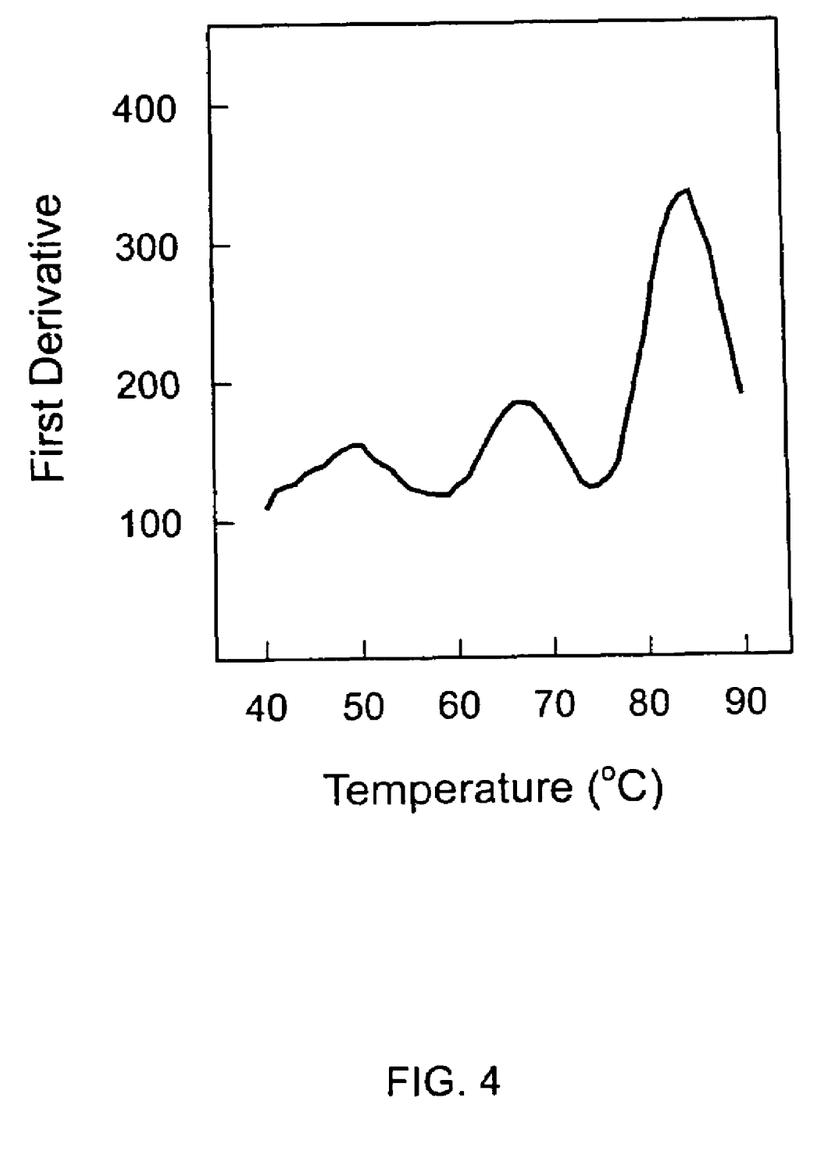
FIG. 4 is the first derivative of a fluorescence curve obtained when a mixture of three signaling hairpin molecules (each of which are labeled with the same fluorophore, and each of which have a different melting temperature) was heated progressively through their three melting temperatures.

Coding schemes according to this invention utilize signaling hairpins having at least two, and for larger arrays three or more, for example four or five, different hairpins that can be distinguished from one another as physical or chemical conditions are changed during the decoding process. As indicated above, a coding scheme of three physically or chemically distinguishable hairpins plus five fluorophores is sufficient for an array of 32,256 different microcarriers. FIG. 4 shows how three identically labeled hairpins are readily distinguishable as temperature is changed. The three signaling hairpins were TM47, TM72, and TM90, all labeled with tetrachlorofluorescein. The first derivative of fluorescence intensity as a function of temperature shows three distinct peaks as the first hairpin opens at about 50° C., then the second hairpin opens at about 67° C., and the third hairpin opens at about 84° C. Fluorescence was measured utilizing an Applied Biosystems 7700 Prism spectrofluorometric thermal cycler. As will be appreciated, continuous readings as a function of temperature are not required. One reading at, say, 40° C., plus three readings at, for example 5° C. above each melting point would have shown the fluorescence intensity jump as each hairpin turned on.

Figure 6A:
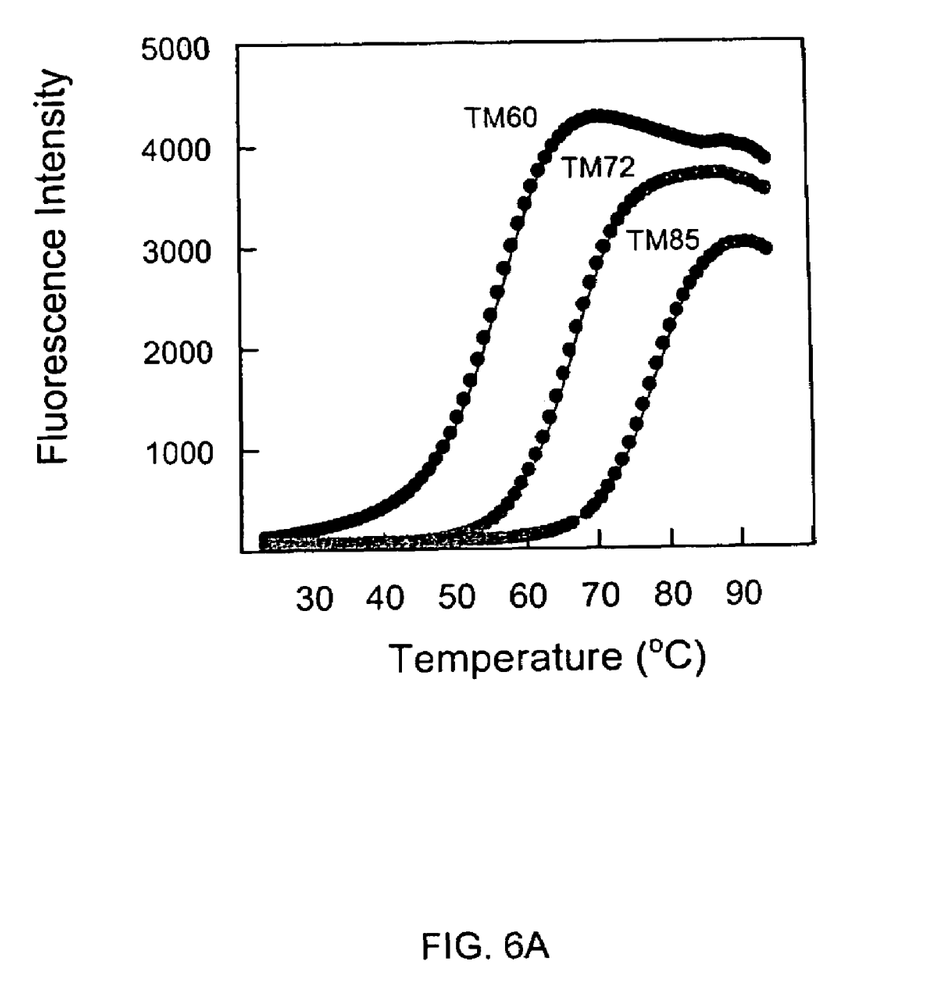
FIGS. 6A-6C compare the behavior of three different signaling hairpins in response to increasing temperature (FIG. 6A), increasing formamide concentration (FIG. 6B), and decreasing guanidine thiocyanate concentration (FIG. 6C).
Figure 6B:
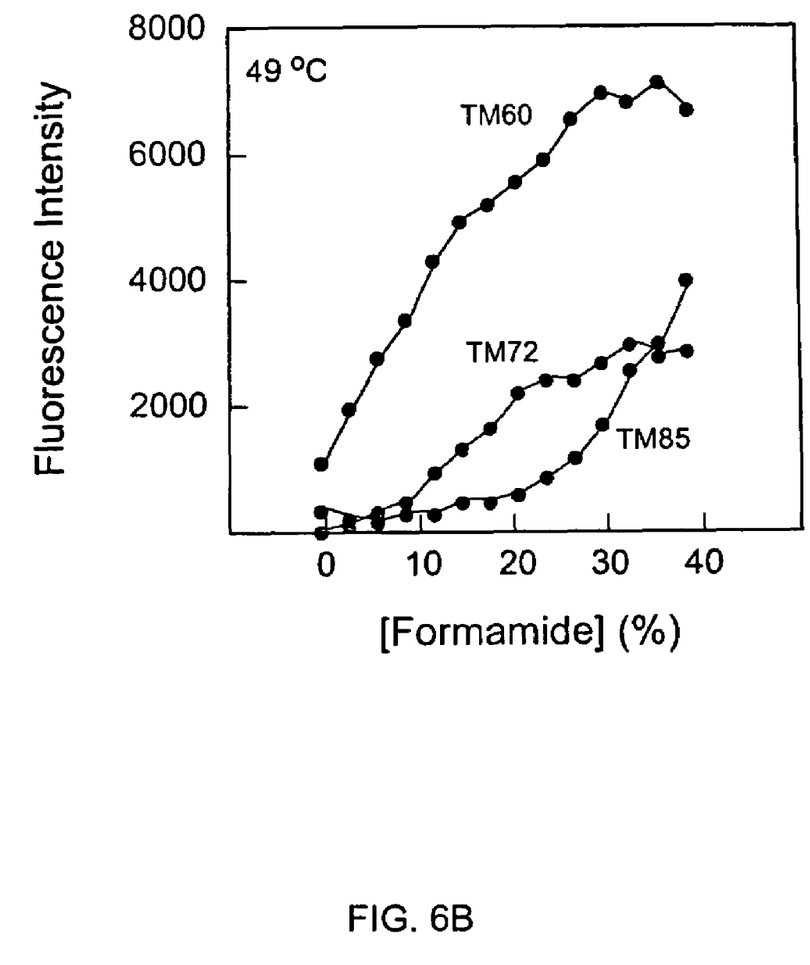
Figure 6C:
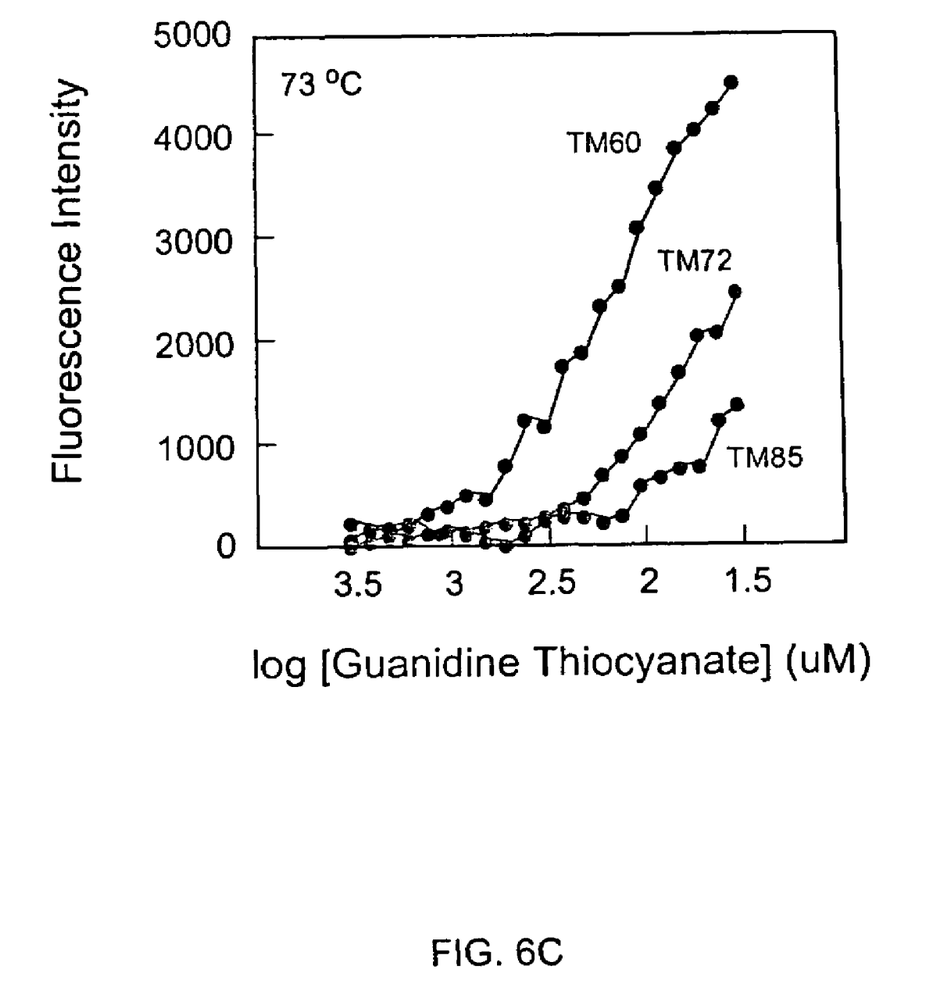

Temperature is an example of one physical or chemical environmental change that can be used to distinguished hairpin-coded microcarriers. Additional examples include addition of formamide in varying concentration and addition of the salt guanidine thiocyanate in varying concentration. A comparison of these three examples is presented in FIGS. 6A-6C. FIG. 6A presents melting curves for three hairpins: TM60, TM72, and TM85, all labeled with tetrachlorofluorescein. As can be seen, the three signaling hairpins melt (in the presence of 4 mM $MgCl_2$, 50 mM KCl, 10 mM Tris-HCl, pH 8.0) at three temperatures about 10° C. apart from one another. With equipment available to us at this time, we are unable to distinguish hairpins having close melting points, but we are able to distinguish reliably hairpins having melting points differing by about 10° C. or more, and we utilize mixtures of such hairpins. FIG. 6B shows fluorescence intensity curves for the same three signaling hairpins at a constant temperature of 49° C. (in the presence of 1 mM $MgCl_2$, 25 mM KCl, 10 mM Tris-HCl, pH 8.0), with increasing amounts of formamide. Even though not optimized for formamide differentiation, three distinct and distinguishable curves were obtained for formamide disruption of the affinity pair. FIG. 6C shows fluorescence intensity curves for the same three signaling hairpins at a constant temperature of 73° C. (in the presence of 10 mM Tris-HCl, pH 8.0), with decreasing amounts of guanidine thiocyanate. In this case, the fluorescence intensity is plotted against the log of the salt concentration. Once again, even though not optimized for guanidine thiocyanate differentiation, three distinct and distinguishable curves were obtained. FIGS. 6B and 6C demonstrate that a change in chemical make-up of the environment can be used to distinguish a plurality (three in this specific example) of signaling hairpin types. These results open up very interesting possibilities for reading and decoding distributed arrays of microcarriers. Environmental conditions that affect the stability of nucleic acid double helices, such as a hairpin stem formed by hybridization of complementary arms, are well know. See, for example, Turner, D. H. (1999) Conformational Changes, appearing as Chapter 8 of Bloomfield, V. A. et al., NUCLEIC ACIDS: STRUCTURE, PROPERTIES, AND FUNCTIONS, University Science Books (Sausalito, California, USA), which discusses effects of changing concentrations of salt ions, such as sodium and magnesium; changing concentrations of co-solvents, such as ethanol and formamide; changing concentrations of other denaturants, such as urea and chaotropic agents; and the effects of changes in temperature and pH. See also Freifelder, D. (1982), PHYSICAL BIOCHEMISTRY, Second Edition, W. H. Freeman and Company (New York, N.Y., USA), at pages 19-29. It will be understood by persons skilled in the art that other affinity pairs are similarly subject to environmental changes, for example, denaturants for antibodies and other proteins. Permanent changes can be used, but these are not preferred, as beads cannot then be reused.

This invention includes a scheme or method for coding microcarriers, such as microbeads, mixtures of coded microcarriers, and arrays and array methods employing such mixtures. As discussed above, from a stock of only three quencher-labeled oligonucleotides and five different fluorophores, one can prepare fifteen different signaling hairpins, which can be immobilized on microbeads in $2^{15}$ different combinations. Using a limited number of fluorophores and a limited number of conditions, for example four fluorophores and two conditions, 256 codes are possible.

Although in our preferred embodiments each different signaling hairpin is coded solely by color and physical property, color intensity can be used in conjunction with color identity in coding schemes of this invention. For example a combination of red and yellow having an intensity ratio of 2:1 can be differentiated from a combination of red and yellow having an intensity ration of 2:2 or 1:2, as is known in the art.

Figure 5:
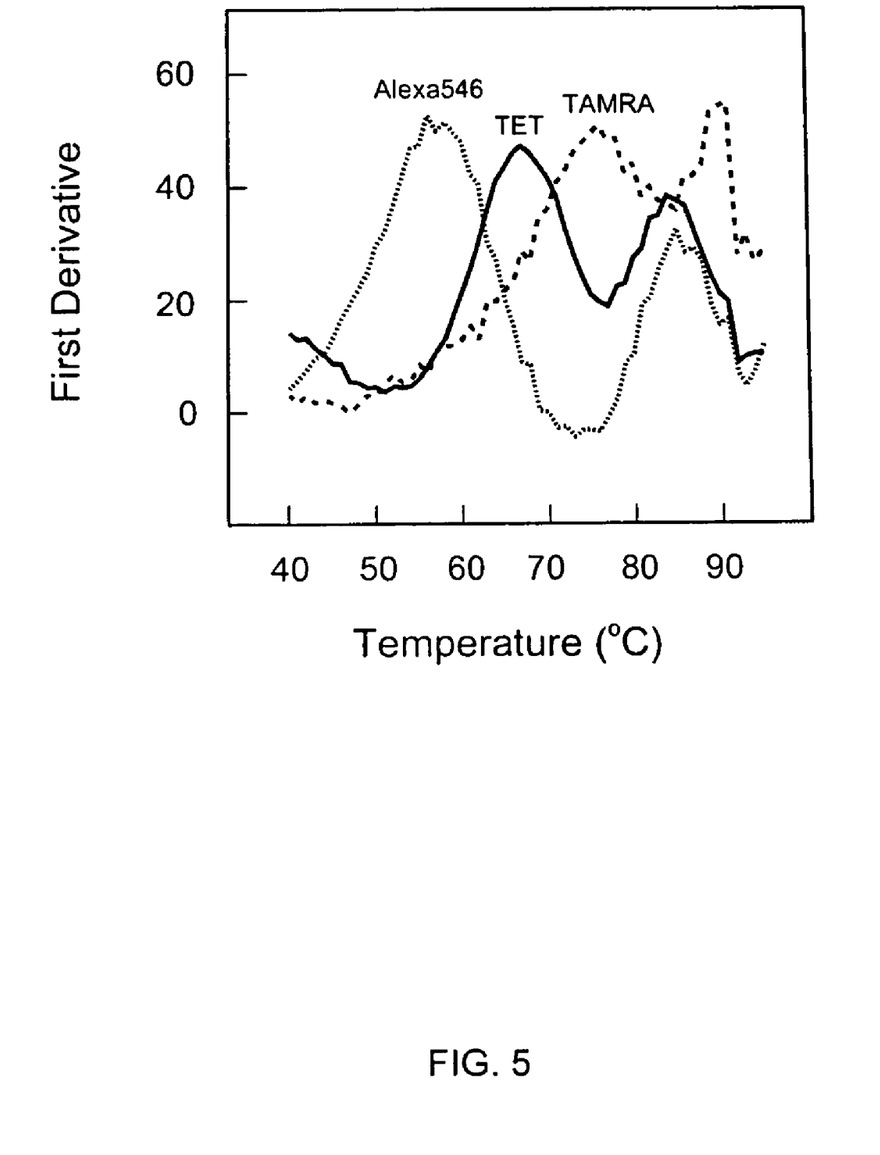
FIG. 5 shows the results obtained with mixture of six different signaling hairpins (two of which were labeled with Alexa 546, two of which were labeled with tetrachlorofluorescein [TET], and two of which were labeled with tetramethylrhodamine [TAMRA]). The complex spectrum obtain at each temperature was deconvolved into the spectrum due to the fluorescence of each of the three fluorophores, and the first derivative of the fluorescence intensity of each fluorophore with respect to temperature was plotted as a function of temperature. The presence of each of the six different signaling hairpins in the mixture is indicated by a peak of fluorescence increase in a particular color at a particular temperature.

FIG. 5 illustrates the deconvolving power of the Applied Biosystems 7700 in our laboratory. This instrument is able to deconvolve a complex spectrum containing as many as seven differently colored fluorophores into the spectra due to the presence of each differently colored fluorophore. In the example shown in FIG. 5, the instrument deconvolved spectra from a mixture of six signaling hairpins, two of which were labeled with Alexa 546, two of which were labeled with tetrachlorofluorescein [TET], and two of which were labeled with tetrametrhylrhodamine [TAMRA], into a curve for each fluorophore showing a peak for each of the two signaling hairpins labeled with the same fluorophore. Simpler systems are possible, as will be recognized. For example, light emitting diodes or filter wheels can be used for stimulation, and filter wheels can be used for detection.

Assays according to this invention may include the steps of contacting an analyte solution containing, or suspected to contain, nucleic acid molecules or fragments thereof with a mixture of microcarriers coded according to this invention, determining which microcarriers hybridized to analyte molecules, or targets, and decoding those microcarriers. Assays may include settling the microcarriers, preferably microbeads, onto a planar surface, for example a microscope slide, as a distributed array prior to determining how much analyte (if any) has hybridized to each microcarrier, and prior to decoding the microcarriers. Assays may include fixing the location of a distributed array of microbeads between two planar surfaces in a flow cell, which is suitable for analyte hybridization after fixation of the array as well as prior to fixation of the array, and which is also suitable for decoding that involves changing the chemical environment, such as adding guanidine thiocyanate in decreasing amounts, either as a gradient or in stepped amounts. As well, assays according to this invention may include capturing a mixture of coded microbeads on the ends of fibers of a fiber-optic bundle either prior to or subsequent to contact with an analyte solution, and determining which fibers have hybridized target. Because decoding arrays according to this invention is so fast and easy, the microbead array need not be permanently affixed to the fiber ends, and decoding can follow fixation. Assays according to this invention may include contacting a mixture of coded microbeads with analyte solution, and then passing beads serially through a flow cytometry system, where each bead is read for hybridization and also decoded. Another option, which has aspects of the flow cell system and the flow cytometry system is to fix the positions of microcarriers into a linear array, as in a capillary tube, through which solutions may be passed, for example, denaturant used for decoding. Any assay method utilizing a distributed array of microbeads or other microcarriers can be utilized with mixtures of microbeads coded according to this invention. Preferred methods include slurrying coded microbeads with analyte solution prior to fixation, to take advantage of liquid phase hybridization kinetics. Chen, J. et al. (2000). Preferred methods also include using multiple copies, for example as many as 20-30 copies, of each microbead to obtain averaged results. Danowski, K. L. and Pantano, P. (2001), Evaluating the Chemical Spatial Resolution of Imaging Fiber Chemical Sensors, Microchem. J. 70: 51-61.

Instrumentation and software of various types are available for performing assays with decodable distributed microarrays. In addition to papers already cited above, see Albert, K. J. et al. (2002), Automatic Decoding of Sensor Types within Randomly Ordered, High-Density Optical Sensor Arrays, Anal. Bioanal. Chem. 373: 792-802; Kellar, K. L. and Iannone, M. A. (2002), Multiplexed Microsphere-Based Flow Cytometric Assays, Exp. Hematol 30: 1227-1237; Tsagkatakis, I. et al. (2001), Spatial and Spectral Imaging of Single Micrometer-Sized Solvent Cast Fluorescent Plasticized Poly(vinylchloride) Sensing Particles, Anal. Chem. 73: 315-320; Walt, D. R. (2000), Bead-Based Fiber-Optic Arrays, Science 287: 451-452; and Yang, L. et al. (2001), BADGE, Beads Arrays for the Detection of Gene Expression, a High Throughput Diagnostic Bioassay, Genome Research 11: 1888-1898. For decoding utilizing temperature change with microscopy, a programmed or programmable variable temperature microscope stage is required. Variable temperature sample holders of various types are well known, and construction of such a microscope stage is within the skill of the art.

A number of embodiments of the invention have been described. Nevertheless, it will be understood that various modifications may be made without departing from the spirit and scope of the invention.

What is claimed is:

1. A hybridization assay for at least one of a multiplicity of nucleic acid sequences in an analyte comprising the steps of:
   (a) contacting said analyte with a mixture of encoded microcarriers having immobilized on their surfaces
      (i) a hybridization probe for one of said multiplicity of sequences, whose hybridization to said at least one sequence can be detected, and
      (ii) a coding scheme comprising a plurality of signaling hairpins that are not hybridization probes for said multiplicity of sequences, including said at least one sequence, comprising quenched, fluorophore-labeled hairpin molecules each comprising an interacting affinity pair separated by a linking moiety, one member of said affinity pair having bound thereto at least one quenched fluorophore, wherein interaction of the affinity pair is disruptable to unquench said at least one fluorophore by a physical or chemical change in a condition of its environment, wherein the disruption of the interaction of at least one affinity pair occurs at a first level of said condition and the disruption of the interaction of at least another affinity pair occurs at a second level of said condition, and wherein said disruptions are optically differentiable, and wherein the coding scheme for identifying individual microcarriers in said mixture comprises a combination of multiple spectrally differentiable fluorophores and multiple affinity pairs disruptable at detectably different levels of said condition;
   (b) forming a distributed array of said microcarriers wherein location of said microcarriers in said distributed array is not used to identify said at least one nucleic acid sequence;
   (c) determining which microcarriers have hybridization probes hybridized to said at least one nucleic acid sequence of said analyte; and
   (d) optically decoding the microcarriers having said at least one nucleic acid sequence hybridized to its hybridization probes to identify said at least one nucleic acid sequence by changing said condition to said detectably different levels to disrupt quenching, and detecting changes in fluorescence from the signaling hairpins.

2. The assay according to claim 1, wherein said interacting affinity pair comprises complementary oligonucleotide sequences hybridized to one another.

3. The assay according to claim 2 wherein said mixture of signaling hairpins includes at least three affinity pairs.

4. The assay according to claim 2 wherein said mixture of signaling hairpins includes from three to eight affinity pairs.

5. The assay according to claim 3 wherein steps (c) and (d) include decoding all microcarriers.

6. The assay according to claim 2, wherein said linking moiety comprises an oligonucleotide sequence.

7. The assay according to claim 2, wherein the step of decoding includes disrupting the hybridized affinity pairs by increasing temperature.

8. The assay according to claim 6, wherein forming the distributed array comprises immobilizing individual microcarriers at the ends of fibers in a fiber-optic bundle.

9. The assay according to claim 2, wherein steps (c) and (d) include flow cytometry.

10. The assay according to claim 2, wherein a quencher is attached to the complementary oligonucleotide sequence not bearing the at least one fluorophore.

11. The assay according to claim 2, wherein step (a) precedes step (b).

12. The assay according to claim 2, wherein step (b) precedes step (a).

13. The assay according to claim 12, wherein said distributed array is a planar array.

14. The assay according to claim 1, wherein the step of forming a distributed array comprises immobilizing individual microcarriers at the ends of fibers in fiber-optic bundles.

15. The assay according to claim 1, wherein step (a) precedes step (b).

16. The assay according to claim 1, wherein step (d) includes disrupting said affinity pairs by increasing temperature.

17. The assay according to claim 1, wherein step (d) includes disrupting said affinity pairs by adding a denaturant.

18. The assay according to claim 1, wherein steps (c) and (d) include flow cytometry.

19. The assay according to claim 1, wherein said distributed array is a planar array.

20. The assay according to claim 1, wherein said distributed array is a linear array.

21. The assay according to claim 1, wherein said hybridization probe is a molecular beacon probe.

22. The assay according to claim 1, wherein step (c) includes determining how much of said at least one nucleic acid sequence has hybridized.

* * * * *

SEQUENCE LISTING

<160> NUMBER OF SEQ ID NOS: 11

<210> SEQ ID NO 1
<211> LENGTH: 24
<212> TYPE: DNA
<213> ORGANISM: Artificial Sequence
<220> FEATURE:
<223> OTHER INFORMATION: synthetically generated oligonucleotide

<400> SEQUENCE: 1
cgctctctct ctgagtctag agcg                                      24

<210> SEQ ID NO 2
<211> LENGTH: 23
<212> TYPE: DNA
<213> ORGANISM: Artificial Sequence
<220> FEATURE:
<223> OTHER INFORMATION: synthetically generated oligonucleotide

<400> SEQUENCE: 2
cgccgtctgt ctgagtctcg gcg                                       23

<210> SEQ ID NO 3
<211> LENGTH: 26
<212> TYPE: DNA
<213> ORGANISM: Artificial Sequence
<220> FEATURE:
<223> OTHER INFORMATION: synthetically generated oligonucleotide

<400> SEQUENCE: 3
cgacctggct gtctgactcc aggtcg                                    26

<210> SEQ ID NO 4
<211> LENGTH: 27
<212> TYPE: DNA
<213> ORGANISM: Artificial Sequence
<220> FEATURE:
<223> OTHER INFORMATION: synthetically generated oligonucleotide

<400> SEQUENCE: 4
cggacgcgct gtctgagtcc gcgtccg                                        27

<210> SEQ ID NO 5
<211> LENGTH: 28
<212> TYPE: DNA
<213> ORGANISM: Artificial Sequence
<220> FEATURE:
<223> OTHER INFORMATION: synthetically generated oligonucleotide

<400> SEQUENCE: 5
ccccgcccta tgtctgagtc gggcgggg                                       28

<210> SEQ ID NO 6
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 6
ggtgctgtct gagtctcacc                                                20

<210> SEQ ID NO 7
<211> LENGTH: 21
<212> TYPE: DNA
<213> ORGANISM: Artificial Sequence
<220> FEATURE:
<223> OTHER INFORMATION: synthetically generated oligonucleotide

<400> SEQUENCE: 7
atgggtgtct gagtctccca t                                              21

<210> SEQ ID NO 8
<211> LENGTH: 28
<212> TYPE: DNA
<213> ORGANISM: Artificial Sequence
<220> FEATURE:
<223> OTHER INFORMATION: synthetically generated oligonucleotide

<400> SEQUENCE: 8
cgctcggtct gtctgagtct atcgagcg                                       28

<210> SEQ ID NO 9
<211> LENGTH: 27
<212> TYPE: DNA
<213> ORGANISM: Artificial Sequence
<220> FEATURE:
<223> OTHER INFORMATION: synthetically generated oligonucleotide

<400> SEQUENCE: 9
aggacgcgct gtctgagtcc gcgtcct                                        27

<210> SEQ ID NO 10
<211> LENGTH: 29
<212> TYPE: DNA
<213> ORGANISM: Artificial Sequence
<220> FEATURE:

-continued

```
<223> OTHER INFORMATION: synthetically generated oligonucleotide

<400> SEQUENCE: 10
ccccgcccgc tgtctgagtc cgggcgggg                                     29

<210> SEQ ID NO 11
<211> LENGTH: 31
<212> TYPE: DNA
<213> ORGANISM: Artificial Sequence
<220> FEATURE:
<223> OTHER INFORMATION: synthetically generated oligonucleotide

<400> SEQUENCE: 11
cgcccgcccg ctgtctgagt ccgggcgggc g                                  31
```